United States Patent
Teng et al.

(10) Patent No.: US 9,726,681 B2
(45) Date of Patent: Aug. 8, 2017

(54) COMPOSITIONS AND METHODS FOR DETECTING CORTISOL

(71) Applicant: Siemens Healthcare Diagnostics Inc., Tarrytown, NY (US)

(72) Inventors: Zhu Teng, Garnet Valley, PA (US); Lauren Seiple, Elkton, MD (US); Martin Drinan, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/910,374

(22) PCT Filed: Aug. 6, 2014

(86) PCT No.: PCT/US2014/049875
§ 371 (c)(1),
(2) Date: Feb. 5, 2016

(87) PCT Pub. No.: WO2015/021108
PCT Pub. Date: Feb. 12, 2015

(65) Prior Publication Data
US 2016/0178650 A1 Jun. 23, 2016

Related U.S. Application Data

(60) Provisional application No. 61/863,020, filed on Aug. 7, 2013.

(51) Int. Cl.
*C07J 41/00* (2006.01)
*G01N 33/74* (2006.01)
*C07K 16/44* (2006.01)

(52) U.S. Cl.
CPC ........ *G01N 33/743* (2013.01); *C07J 41/0016* (2013.01); *C07K 16/44* (2013.01); *C07B 2200/11* (2013.01)

(58) Field of Classification Search
CPC ... C07K 16/44; C07J 41/0016; G01N 33/743; C07B 2200/11
See application file for complete search history.

(56) References Cited

U.S. PATENT DOCUMENTS

| | | |
|---|---|---|
| 5,910,575 A | 6/1999 | Lupi-Chen et al. |
| 2006/0105472 A1 | 5/2006 | Teng et al. |

(Continued)

OTHER PUBLICATIONS

International Search Report and Written Opinion of International Application No. PCT/US2014/049875 dated Oct. 27, 2014.

(Continued)

*Primary Examiner* — Shafiqul Haq
(74) *Attorney, Agent, or Firm* — Cynthia G. Tymeson

(57) ABSTRACT

Methods of detecting Cortisol in samples suspected of containing Cortisol are disclosed that utilize conjugates of 11-a-cortisol linked at the 3-position to an assay molecule. In addition, compounds are disclosed that have the formula: (structure) wherein L is a linking group and X is as further defined herein.

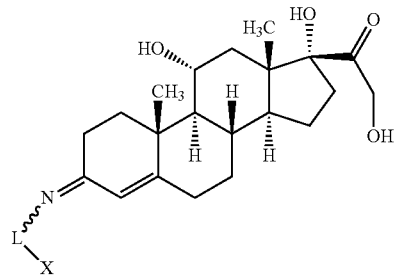

9 Claims, 4 Drawing Sheets

(56) References Cited

U.S. PATENT DOCUMENTS

| | | | |
|---|---|---|---|
| 2006/0172356 A1* | 8/2006 | Ouyang | C07D 253/075 435/7.92 |
| 2007/0178543 A1 | 8/2007 | Self | |
| 2012/0045847 A1 | 2/2012 | Lewisch et al. | |
| 2013/0078739 A1* | 3/2013 | Kasagi | G01N 33/553 436/501 |

OTHER PUBLICATIONS

No Author, PubChem, Compound Summary for: CID 13767341, Cortisol 3-(O-carboxymethyl)oxime; 2007: 1-21 <https://pubchem.ncbi.nlm.nih.gov/summary/summary.cgi?cid=13767341(Sep. 24, 2014 7: 14:29 AM>.

* cited by examiner

11-β-cortisol

11-α-cortisol

COMPOSITIONS AND METHODS FOR DETECTING CORTISOL

BACKGROUND

This invention relates to compositions, methods and kits for determining a presence and/or an amount of cortisol including analogs and metabolites thereof in a sample suspected of containing the same. The invention also relates to methods of improving signal separation and low end sensitivity, accuracy and precision in methods for determining an amount of cortisol in samples suspected of containing cortisol.

Cortisol, or hydrocortisone, is a steroid hormone, more specifically a glucocorticoid hormone. Cortisol is synthesized enzymatically in the body from cholesterol, produced by the *zona fasciculata* of the adrenal cortex. Release of cortisol is controlled by the hypothalmus, usually in response to stress and a low level of blood glucocorticoids. The primary functions of cortisol are to increase blood sugar through gluconeogenesis, suppress the immune system, and aid in fat, protein and carbohydrate metabolism. Cortisol can also result in a decrease of bone formation. In blood, cortisol is bound for the most part by endogenous binding substances such as, for example, certain proteins in the blood. These binding substances include, but are not limited to, corticosteroid binding globulin, albumin and testosterone and estradiol binding globulin, for example.

Assessing cortisol levels in biological samples is important since various synthetic forms of cortisol are used to treat a variety of diseases and since cortisol levels in samples from mammals may provide relevant information regarding, by way of illustration and not limitation, hypercortisolism (Cushing's syndrome), hyperadrenocorticism, proteolysis, muscle wasting, chronic subtle percortisolism (potbelly syndrome), and hypocortisolism (Addison's disease), for example. Furthermore, cortisol may be employed therapeutically to prevent release of substances in the body that cause inflammation, for example.

There is a need for reagents and methods for accurate and sensitive determinations of concentrations of cortisol and analogs and metabolites thereof in samples.

SUMMARY

Some examples in accordance with the principles described herein are directed to a compound of the formula:

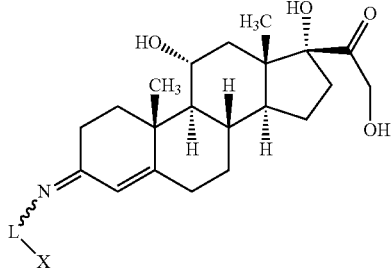

wherein:
L is a linking group and X is —OH, —COOH, —COO—N-hydroxysuccinimide, a support, a member of a signal producing system or a member of a specific binding pair.

Some examples in accordance with the principles described herein are directed to a compound of the formula:

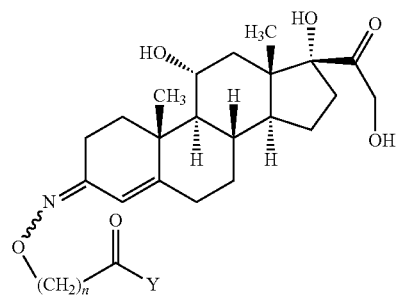

wherein:
n is an integer of 1 to 10 and Y is —OH, N-hydroxysuccinimide, a member of a signal producing system, a member of a specific binding pair, a support, or —NH—$R^2$ wherein $R^2$ is a support, a member of a signal producing system or a member of a specific binding pair.

Some examples in accordance with the principles described herein are directed to methods of determining in a sample the presence and/or amount of cortisol. The method comprises providing in combination in a medium a sample suspected of containing cortisol, a specific binding member for cortisol and a conjugate of 11-α-cortisol linked at the 3-position to an assay molecule. The combination is subjected to conditions for binding of the conjugate to the specific binding member for cortisol to form a complex. The amount of the complex is measured and the amount of the complex is related to the presence and/or amount of cortisol in the sample.

Some examples in accordance with the principles described herein are directed to methods of determining in a sample the presence and/or amount of cortisol. The method comprises providing in combination in a medium a sample suspected of containing cortisol, a specific binding member for cortisol and a compound of the formula:

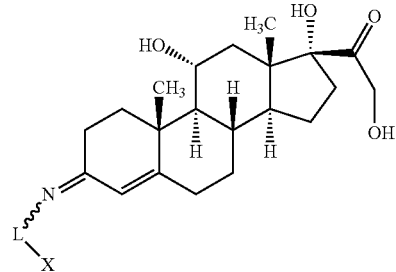

wherein L is a linking group and X is a support or a member of a signal producing system. The combination is subjected to conditions for binding of the compound to the specific binding member for cortisol to form a complex. The amount of the complex is measured and the amount of the complex is related to the presence and/or amount of cortisol in the sample.

BRIEF DESCRIPTION OF DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION OF SPECIFIC EMBODIMENTS

General Discussion

Figure 1:
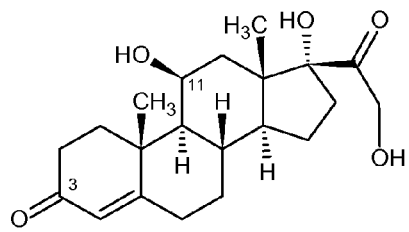
FIG. 1 is a depiction of the structure of 11-β-cortisol.
Figure 2:
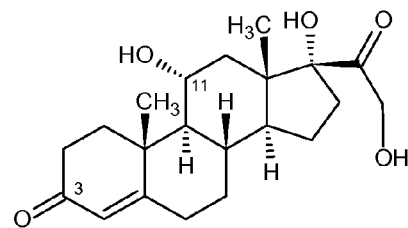
FIG. 2 is a depiction of the structure of 11-α-cortisol.

Conjugates of 11-α-cortisol are useful in methods of detecting cortisol in samples suspected of containing cortisol. The present inventors have found that conjugates of 11-α-cortisol conjugated at the 3-position to an assay molecule, when used in an assay for cortisol, exhibit enhanced assay results when compared to the use of conjugates of 11-β-cortisol and an assay molecule in such assays. The assay molecule may be conjugated to the 11-α-cortisol by a direct bond or through the intermediacy of a linking group. The phrase "assay molecule" refers to any molecule that is employed as part of an assay for the determination of a cortisol analyte in a sample suspected of containing such analyte. In some examples, the assay molecule is a member of a specific binding pair (sbp), or a member of a signal producing system (sps), for example. In some examples, the linking group comprises an imine functionality wherein the nitrogen atom of the imine functionality is linked to an atom selected from the group consisting of oxygen and carbon, for example. In some examples, the linking group in conjunction with the 3-position of the 11-α-cortisol comprises a ketoxime functionality, which may be in a stereoisomeric form, either the syn-isomer or the anti-isomer, or a combination of both forms. In some examples, the stereoisomeric form of the ketoxime is the syn-isomer.

As mentioned above, some examples in accordance with the principles described herein are directed to compounds of the formula:

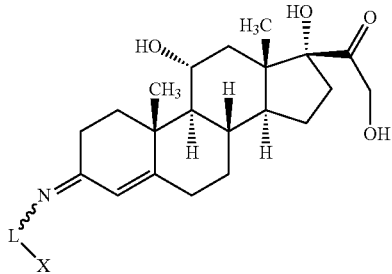

wherein:
L is a linking group and X is —OH, —COOH, —COO—N-hydroxysuccinimide, a support, a member of a signal producing system or a member of a specific binding pair. In the above formula, the N-L bond may be in a stereoisomeric form, either the syn-isomer or the anti-isomer, or a combination of both forms. In some examples, the stereoisomeric form of the N-L bond is the syn-isomer.

In some examples in accordance with the principles described herein, the linking group has a molecular weight less than about 2000, or less than about 1500, or less than about 1000, or less than about 500, or less than about 300, or less than about 200, or less than about 150, for example, but more than about 25. Molecular weight is defined as the sum of the atomic weights of all the atoms in a molecule and may also be referred to as the formula weight. The linking group may comprise about 2 to about 200 atoms, or 4 to about 150 atoms, or about 5 to about 100 atoms, or about 5 to about 50 atoms, or about 5 to about 25 atoms, not counting hydrogen, and may comprise a chain of from 2 to about 100 atoms, or 3 to about 90 atoms, or about 4 to about 80 atoms, or about 5 to about 70 atoms, or about 10 to about 50 atoms, or about 10 to about 25 atoms, or about 5 to about 20 atoms, or about 5 to about 10 atoms, for example, each independently selected from the group consisting of carbon, oxygen, sulfur, nitrogen, and phosphorous, usually carbon and oxygen. The number of heteroatoms in the linking group is dependent on the size of the linking group and, in some examples, the number of heteroatoms is in the range of from 0 to about 30, or 1 to about 25, or about 2 to about 20, or about 2 to about 15, or about 2 to about 10, or about 3 to about 10, or about 3 to about 5, for example. The atoms of the linking group may be substituted with atoms other than hydrogen such as, for example, one or more of carbon, oxygen and nitrogen in the form of, e.g., alkyl, aryl, aralkyl, hydroxyl, alkoxy, aryloxy, or aralkoxy groups. As a general rule, the length of a particular linking group can be selected arbitrarily to provide for convenience of synthesis with the proviso that there is minimal interference caused by the linking group with the ability of the linked molecules to perform their particular function such as, for example, their function in an assay. The linking group may be aliphatic or aromatic.

The heteroatoms may be in the form of one or more functionalities including, but not limited to, one or more of amine (primary, secondary or tertiary), oxime, carbamate, ether, ester, amide, urea, sulfonamide, thioether, hydrazone, hydrazide, amidine, and phosphate ester, for example. In one example in accordance with the principles described herein, the linking group comprises two nitrogen atoms in the form of secondary amine functionalities and one carbonyl group in a chain of about 6 to about 20, or about 6 to about 15, or about 6 to about 10, or about 7 to about 20, or about 7 to about 15, or about 7 to about 10, or about 7 to about 9, or about 7 to about 8, or about 7 atoms, which number of atoms includes carbon atoms.

In some examples the linking group is —O—$(CH_2)_p$—C(O)—$(W)_b$—$(CH_2)_q$—$(X)_c$—$(CH_2)_r$— wherein W and X are each independently —NH— or —O—, b and c are each independently 0 or 1, p is an integer of 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example; q is an integer of, 0 to 10, or 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example; and r is an integer of 1 to 10, or 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example.

In some examples, b, q, c, and r in the above formula are 0, and p=n, and the linking group (L) has the formula —O—$(CH_2)_n$CO— wherein n is an integer of 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example. In some examples where L is —O—$(CH_2)_n$CO—, X is H, N-hydroxysuccinimide, a member of a signal producing system, a member of a specific binding pair, a support, or —NH—$R^2$ wherein $R^2$ is a support, a member of a signal producing system or a member of a specific binding pair.

In some examples the linking group is —$(CH_2)_m$— wherein m is an integer of 1 to 12, or 1 to 11, or 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example. In some examples where L is —$(CH_2)_m$—, X is a member of a signal producing system, a member of a specific binding pair, a support, or —NH—$R^2$ wherein $R^2$ is a support, a member of a signal producing system or a member of a specific binding pair.

The signal producing system may have one or more members, at least one member being a label. The signal producing system generates a signal that relates to the amount of cortisol in a sample. The signal producing system includes all of the reagents required to produce a measurable signal. In some examples, the signal producing system includes particles, fluorescent compounds, chemiluminescent compounds, sensitizers, enzymes, and radiolabels, by way of illustration and not limitation. Other components of the signal producing system may be included in a developer solution and can include, but are not limited to, substrates, enhancers, activators, chemiluminescent compounds, cofactors, inhibitors, scavengers, metal ions, and specific binding substances required for binding of signal generating substances, for example. Other components of the signal producing system may be coenzymes, substances that react with enzymic products, other enzymes and catalysts, for example. The signal producing system provides a signal detectable by external means, by use of electromagnetic radiation, desirably by visual examination. Exemplary signal-producing systems are described in U.S. Pat. No. 5,508,178, the relevant disclosure of which is incorporated herein by reference.

The term "label" includes poly(amino acid) labels and non-poly(amino acid) labels. The term "poly(amino acid) label moieties" includes labels that are proteins such as, but not limited to, enzymes, antibodies, peptides, and immunogens, for example. With label proteins such as, for example, enzymes, the molecular weight range will be from about 10,000 to about 600,000, or from about 10,000 to about 300,000 molecular weight. There is usually at least one compound in accordance with the principles described herein (analog group) per about 200,000 molecular weight, or at least about 1 per about 150,000 molecular weight, or at least about 1 per about 100,000 molecular weight, or at least about 1 per about 50,000 molecular weight, for example, of the protein. In the case of enzymes, the number of analog groups is usually from 1 to about 20, about 2 to about 15, about 3 to about 12, or about 6 to about 10.

Enzymes include, by way of illustration and not limitation, redox enzymes such as, for example, dehydrogenases, e.g., glucose-6-phosphate dehydrogenase and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example.

The term "non-poly(amino acid) labels" includes those labels that are not proteins. The non-poly(amino acid) label is capable of being detected directly or is detectable through a reaction that produces a detectable signal. The non-poly (amino acid) label can be isotopic or non-isotopic and can be, by way of illustration and not limitation, a radioisotope, a luminescent compound (which includes, but is not limited to acridinium esters, fluorescent compounds and chemiluminescent compounds, for example), a polynucleotide coding for a catalyst, a promoter, a dye, a coenzyme, an enzyme substrate, a radioactive group, and an amplifiable polynucleotide sequence, for example. In some example, the non-poly (amino acid) labels are radioisotopic, luminescent (such as, e.g., acridinium esters), particulate (such as, e.g., magnetic particles that can be separated bound from un-bound, latex particles that can be measured by turbidity and nephelometry, and chemiluminescence beads (e.g., LOCI chemibeads), for example.

Magnetic particles include paramagnetic particles, ferromagnetic particles and diamagnetic particles. Such particles include, but are not limited to, transition metals of periods 4-7 of the Periodic Table including chromium, copper, cobalt, aluminum, manganese, iron, and nickel, for example.

Chemiluminescent particles are particles that have associated therewith a chemiluminescent compound. The phrase "associated therewith" as used herein means that a compound such as, for example, a chemiluminescent compound and a particle may be associated by direct or indirect bonding, adsorption, absorption, incorporation, or solution, for example. Examples of chemiluminescent compounds that may be utilized are those set forth in U.S. Pat. Nos.

5,340,716 and 6,251,581, the relevant disclosures of which are incorporated herein by reference. In some examples in accordance with the principles described herein, the chemiluminescent compound is a photoactivatable substance that undergoes a chemical reaction upon direct or sensitized excitation by light or upon reaction with singlet oxygen to form a metastable reaction product that is capable of decomposition with the simultaneous or subsequent emission of light, usually within the wavelength range of 250 to 1200 nm. The term "photoactivatable" includes "photochemically activatable". In some examples, the chemiluminescent compounds are those that react with singlet oxygen to form dioxetanes or dioxetanones. The latter are usually electron rich olefins. Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, and luminol. Examples of such chemiluminescent compounds that may be utilized are those set forth in U.S. Pat. No. 5,709,994, the relevant disclosure of which is incorporated herein by reference.

Sensitizer particles are particles that have associated therewith a sensitizer compound, which includes, but is not limited to, a photosensitizer compound. Examples of sensitizer compounds that may be utilized are those set forth in U.S. Pat. Nos. 5,340,716 and 6,251,581, the relevant disclosures of which are incorporated herein by reference.

A photosensitizer is a sensitizer for generation of singlet oxygen usually by excitation with light. In some examples, the photosensitizer absorbs at a longer wavelength than the chemiluminescent compound and has a lower energy triplet than the chemiluminescent compound. The photosensitizer can be photoactivatable (e.g., dyes and aromatic compounds). The photosensitizer is usually a compound comprised of covalently bonded atoms, usually with multiple conjugated double or triple bonds. The compound should absorb light in the wavelength range of 200-1100 nm, usually 300-1000 nm, preferably 450-950 nm. Typical photosensitizers include, but are not limited to, acetone, benzophenone, 9-thioxanthone, eosin, 9,10-dibromoanthracene, methylene blue, metallo-porphyrins (e.g., hematoporphyrin), phthalocyanines, chlorophylls, rose bengal, buckminsterfullerene, for example, and derivatives of these compounds. Examples of other photosensitizers are enumerated in N. J. Turro, "Molecular Photochemistry", page 132, W. A. Benjamin Inc., N.Y. 1965. The photosensitizer assists photoactivation where activation is by singlet oxygen. Usually, the photosensitizer absorbs light and the thus formed excited photosensitizer activates oxygen to produce singlet oxygen, which reacts with the chemiluminescent compound to give a metastable luminescent intermediate.

The specific binding member is a member of a specific binding pair, which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, for example, are not immunological pairs but are included within the scope of the term "sbp member."

Specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

In some examples of assays in accordance with the principles described herein, the specific binding member is an antibody, which may be a complete immunoglobulin molecule or a fragment thereof. Antibodies include various classes and isotypes, such as IgA, IgD, IgE, IgG1, IgG2a, IgG2b and IgG3, and IgM, for example. Fragments thereof may include Fab, Fv and $F(ab')_2$, Fab', and the like. In addition, aggregates, polymers, and conjugates of immunoglobulins or their fragments are included within the term "antibody" where appropriate so long as binding affinity for an analyte is retained. Antibodies may be prepared by techniques including, but not limited to, immunization of a host and collection of sera (polyclonal), preparing continuous hybrid cell lines and collecting the secreted protein (monoclonal) or cloning and expressing nucleotide sequences or mutagenized versions thereof coding at least for the amino acid sequences required for specific binding of natural antibodies, for example.

As mentioned above, in some examples in accordance with the principles described herein, an sbp member may be a small organic molecule of molecular weight of about 200 to about 2,000, or about 200 to about 1,500, or about 200 to about 1,000, or about 200 to about 500. Such small organic molecules include, but are not limited to, biotin, fluorescent molecules (such as fluorescein and rhodamine, for example), chemiluminescent molecules, and dinitrophenol, for example. The sbp member may be a binding partner for a small organic molecule, that is, a molecule that specifically recognizes and binds to the small molecule. Binding partners for a small molecule are defined by the nature of the small molecule and include, but are not limited to, avidin, streptavidin, antibody for the small organic molecule (which include, but are not limited to, antibody for a fluorescent molecule (such as antibody for fluorescein and antibody for rhodamine, for example), antibody for a chemiluminescent molecule, and antibody for dinitrophenol, for example.

The "support" may be comprised of an organic or inorganic, solid or fluid, water insoluble material and which may be transparent or partially transparent. The support can have any of a number of shapes, such as, but not limited to, a particle (particulate support) including bead, a film, a membrane, a tube, a well, a strip, a rod, a fiber, or a planar surface such as, e.g., a plate or paper, for example. The support may or may not be suspendable in the medium in which it is employed. Examples of suspendable supports are polymeric materials such as latex, lipid bilayers or liposomes, oil droplets, cells and hydrogels, and magnetic particles, for example. Other support compositions include polymers, such as, by way of illustration and not limitation, nitrocellulose, cellulose acetate, poly (vinyl chloride), polyacrylamide, polyacrylate, polyethylene, polypropylene, poly(4 methylbutene), polystyrene, polymethacrylate, poly(ethylene terephthalate), nylon, poly(vinyl butyrate), for example, either used by themselves or in conjunction with other materials. The support may or may not be further labeled with a dye, catalyst or other detectable group, for example.

In some examples in accordance with the principles described herein, the support may be a particle. The particles have an average diameter of at least about 0.02 microns and not more than about 100 microns. In some examples, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus*, and *E. coli*, viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chromium dioxide (chrome) particles or latex particles.

Some examples in accordance with the principles described herein are directed to compounds of the formula:

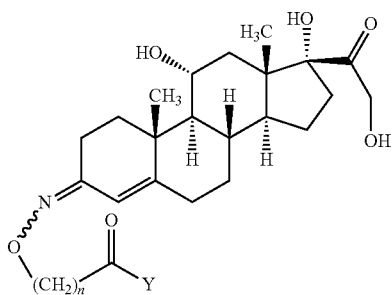

wherein:

n is an integer of 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, and Y is —OH, N-hydroxysuccinimide, a member of a signal producing system, a member of a specific binding pair, a support, or —NH—$R^2$ wherein $R^2$ is a support, a member of a signal producing system or a member of a specific binding pair.

Preparation of Compounds

Examples of methods of preparing compounds in accordance with the principles described herein are described, by way of illustration and not limitation. Other approaches may be employed to form the compounds consistent with the principles described herein. The method of preparing conjugates of 11-α-cortisol and an assay molecule for use in methods for detecting cortisol in accordance with the principles described herein are dependent on the nature of the reaction to be carried out using the ketone oxygen at the 3-position of 11-α-cortisol.

Figure 3:
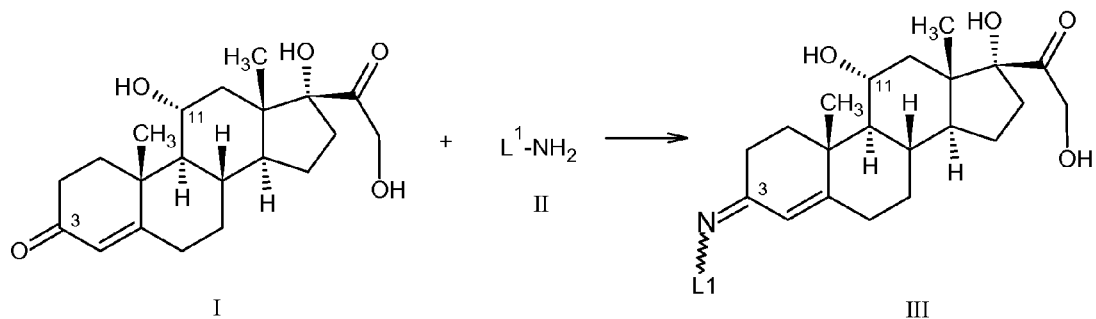
FIG. 3 is a schematic depiction of the synthesis of an example of compounds in accordance with the principles described herein.

In some examples, the methods of preparing such compounds include reaction of the ketone oxygen at the 3-position of 11-α-cortisol with an amine to form an imine. This reaction is depicted in FIG. 3. Amine II ($L^1$-$NH_2$) comprises $L^1$, which may be —OH, for example, or may comprise all or part of a linking group to which an assay molecule is, or will be, linked. In some examples, $L^1$ comprises one or more reactive functional groups for linking to an assay molecule. Functional groups on $L^1$ or on an assay molecule, e.g., sbp member or sps member, or both may be present naturally or may be introduced synthetically and are discussed more fully below. Such reactive functional groups or functionalities include, by way of illustration and not limitation, aldehyde, carboxy, amino, imino, sulfhydryl and hydroxy, for example. A large number of suitable functional groups are available for attaching to amino groups (amine reactive functional groups), carboxy groups (carboxy reactive functional groups), sulfhydryls (sulfhydryl reactive functional groups), and alcohols (alcohol reactive functional groups), for example. Such functional groups include, but are not limited to, activated esters including, e.g., carboxylic esters, imidic esters, sulfonic esters and phosphate esters; thioesters; amides; thioamides; ethers; ureas; thioureas; guanidines; azo groups; thioethers; carboxylate activated nitrites; aldehydes; ketones; maleimides; haloalkylamides; and alkylating agents, for example. In some examples, $L^1$ is —O—$(CH_2)_n$COH wherein n is as defined above, for example. Conditions, such as, for example, temperature and duration, for the reaction of compound I with $L^1$-$NH_2$ are dependent on the nature of $L^1$, for example.

Figure 4:
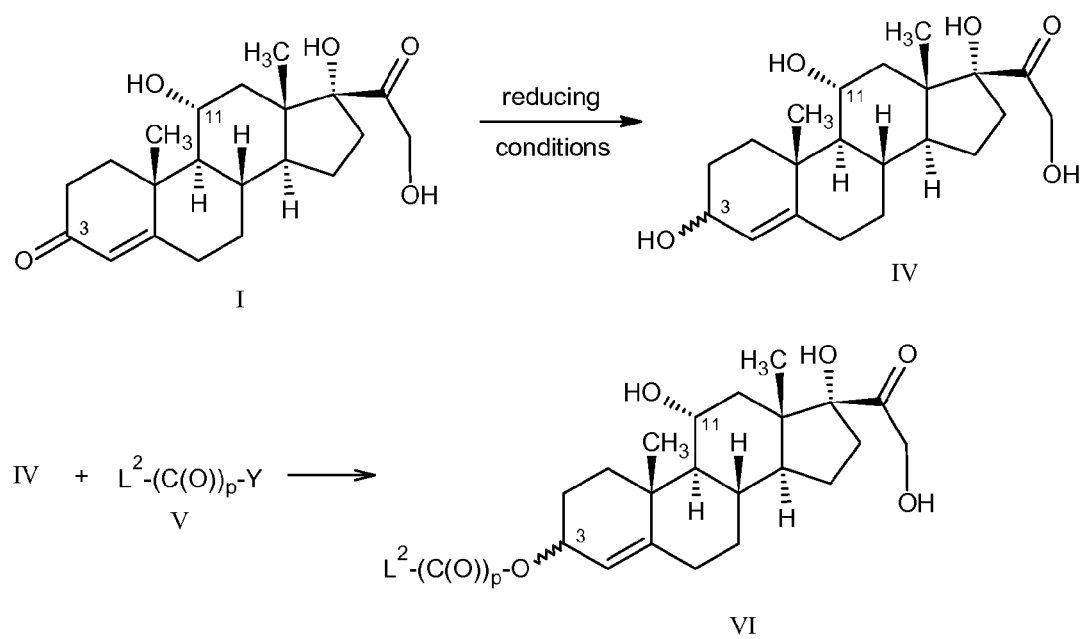
FIG. 4 is a schematic depiction of the synthesis of another example of compounds in accordance with the principles described herein.

In some examples, the methods of preparing such compounds include reduction of the ketone oxygen at the 3-position of 11-α-cortisol to a hydroxy group, which then may be alkylated (forming an ether functionality), or esterified, for example. FIG. 4 depicts an example of a reaction in accordance with the above. Prior to the reduction of the ketone at the 3-position as depicted in FIG. 4, the hydroxy groups of compound I (11-α-cortisol) are protected (not shown in FIG. 4) using a suitable protecting group such as a silyl group, which may be, for example, a trimethylsilyl group, a t-butyldiphenylsilyl group, a t-butyldimethylsilyl group or a triisopropylsilyl group. Compound I is treated under reducing conditions to obtain compound IV having a hydroxy group at the 3-position. Such reducing conditions include, by way of illustration and not limitation, treating the cortisol with a metal hydride such as, for example, $LiAlH_4$ or $NaBH_4$. The reactions are usually carried out in solution in an ether such as, for example, a dialkyl ether, e.g., diethyl ether; dioxene, or tetrahydrofuran; or mixtures of two or more thereof. The solvent should be dried thoroughly. The reaction is carried out at a temperature of about 15° C. to about 30° C., or about 20° C. to about 25° C. or at room temperature.

Compound IV is then reacted with $L^2$-$C(O))_p$—Y (compound V) to give compound VI. In compound V; p is 0 or 1; Y is activated ester, halogen (chorine, bromine, fluorine or iodine), or anhydride, for example, when p is 1; and Y is activated ester, or halogen, for example, when p is 0; and $L^2$ may comprise all or part of a linking group to which an assay molecule is, or will be, linked. In some examples, $L^2$ comprises one or more reactive functional groups for linking to an assay molecule. Such functional groups are those listed above for $L^1$. Conditions, such as, for example, temperature and duration, for the reaction of compound IV with $L^2$-$(C(O))_p$—Y are dependent on one or more of the nature of $L^2$, the nature of Y, and whether p is 0 or 1, for example. Then, the protecting groups are removed (not shown in FIG. 4) using a suitable deprotection agent, the nature of which depends on, for example, the nature of p. In some examples the removal of the protecting groups may be carried out, for example, under acidic conditions.

Figure 5:
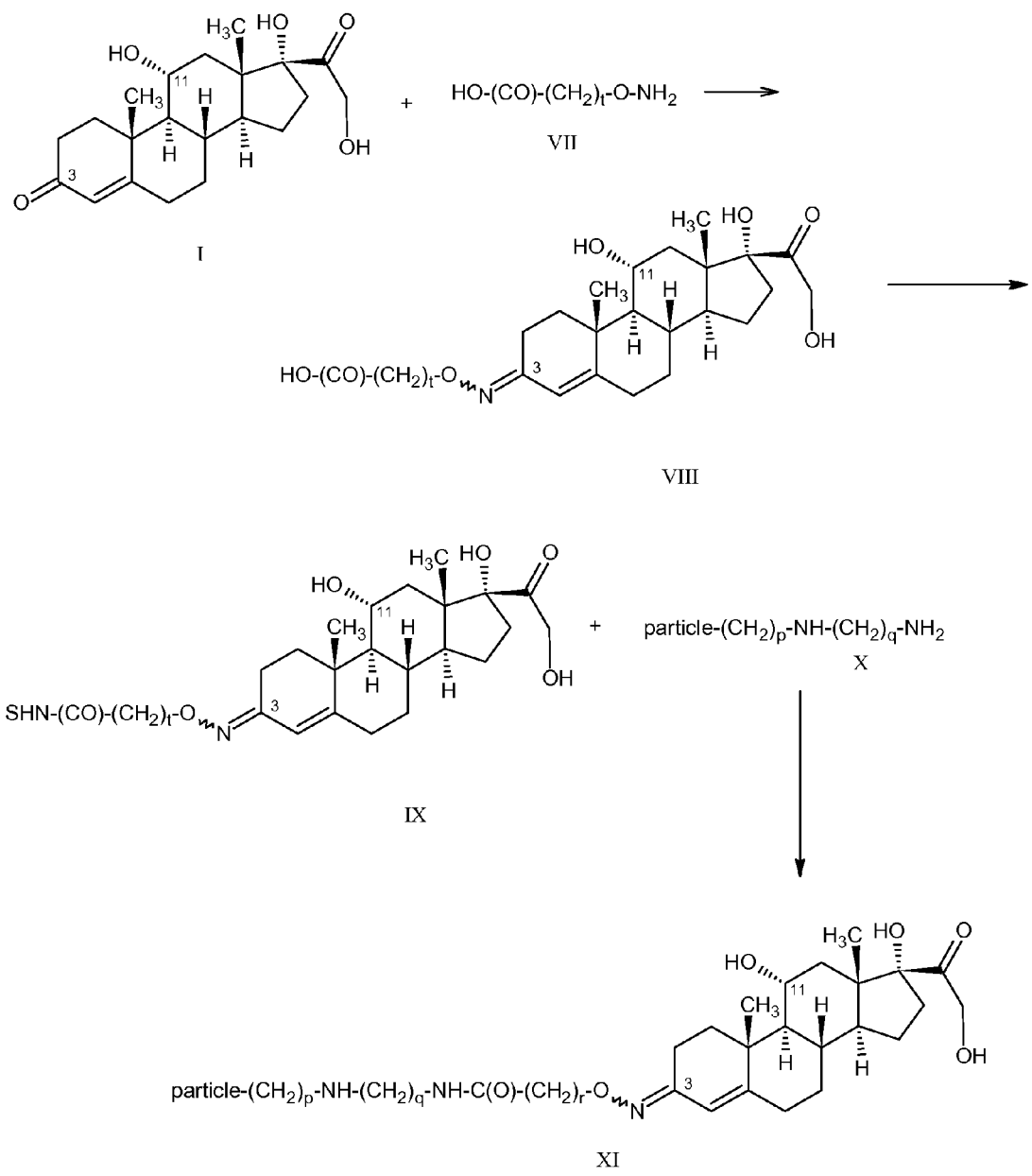
FIG. 5 is a schematic depiction of the synthesis of another example of compounds in accordance with the principles described herein.

In one example in accordance with the principles described herein, referring to FIG. 5, 11-α-cortisol (compound I) is reacted with compound VII to give compound VIII wherein t is an integer of 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example. In some examples, t is 1 and compound VII is carboxymethoxyamine (e.g., carboxymethoxylamine hemihydrochloride (CMO)). The reaction is carried out in a polar organic solvent such as, for example, an alcohol of 1 to 5 carbon atoms ($C_1$-$C_5$ alcohol), an ether, an amide, a nitrile, a haloalkane, or a sulfoxide, for example, or a mixture of two or more of the above. In some examples, the solvent is anhydrous. The anhydrous polar organic solvent may be, for example, methanol, acetonitrile, dichloromethane, tetrahydrofuran (THF), dimethylformamide (DMF) or dimethylsulfoxide (DMSO). The temperature during the reaction is about 18° C. to about 25° C., or about room temperature. The reactants are subjected to agitation during the reaction by stirring or shaking, for example. The time period of the reaction is about 2 hours to about 24 hours, or about 15 to about 22 hours, for example. The reaction is conducted in the presence of a weak base such as, for example, sodium acetate, triethylamine, or diisopropylethylamine, for example, or mixtures of two or more thereof.

Compound VIII is treated to activate the carboxy group for coupling to a linking group and/or an assay molecule. Activation may be achieved by, for example, treatment with one or more of a carbodiimide, N-hydroxysuccimimide, and sulfo-N-hydroxysuccinimide, for example. In some examples, the carboxy group of compound VIII is activated by formation of sulfo-NHS ester IX. The reaction is carried out by combining compound VIII with an activation agent such as, for example, sulfo-NHS, in the presence of, for example, 1-ethyl-3-(3-dimethylaminopropyl)carbodiimide (EDAC) in an anhydrous polar organic medium such as, for example, DMSO, at a temperature of about 15° C. to about 40° C., or about 20° C. to about 30° C., or at ambient temperature for a period of about 10 hours to about 25 hours, or about 12 hours to about 20 hours, or about 18 hours. The medium is subjected to agitation such as by rotating or stirring, for example. The organic solvent may, but need not, be removed by evaporation, which may be accelerated by subjecting the contents of the reaction vessel to a vacuum. The residue may be combined with a polar organic solvent such as, for example, ethyl acetate or dichloromethane and then washed with an aqueous solution of an inorganic salt such as, for example, brine or sodium bicarbonate solution. The organic phase may be dried by, for example, mixing with an anhydrous inorganic salt such as, sodium sulfate or magnesium sulfate, for example. Following drying, the organic phase may be treated to separate any solid material by subjecting the organic phase to, for example, filtration or decantation. The organic solvent is removed by evaporation, which may be accelerated by subjecting the contents of the reaction vessel to a vacuum. The resulting dry product may be purified by chromatographic means such as, for example, high performance liquid chromatography (HPLC), reverse phase liquid chromatography (RPLC), high turbulence liquid chromatography (HTLC), or gas chromatography. The product may be stored in an anhydrous polar organic solvent such as, for example, DMSO or DMF.

Referring to FIG. 5, a particle such as, for example, a latex particle having incorporated therein a chemiluminescent compound (dye) and having an inner aminodextran layer and an outer dextran aldehyde layer is prepared by a procedure similar to that described in U.S. Pat. No. 7,179,660, the relevant disclosure of which is incorporated herein by reference. Aldehyde groups on the outer dextran aldehyde layer are reacted with ethylene diamine under reductive amination conditions to form reagent X, which is a particle reagent having pendant moieties comprising a terminal amine group. The reductive amination conditions include the use of a reducing agent such as, for example, a metal hydride (e.g., sodium borohydride or potassium borohydride), sodium cyanoborohydride, or sodium triacetoxyborohydride. The reaction is carried out in an aqueous medium at a temperature during the reaction of about 20° C. to about 100° C., or about 30° C. to about 50° C., for a period of about 1 hour to about 48 hours, or about 5 hours to about 24 hours. The point of linkage of the pendant moieties with the outer dextran aldehyde layer comprises a secondary amine linkage.

Sulfo-NHS ester IX (in an anhydrous polar organic solvent such as, for example, DMSO or DMF) is combined with particle reagent X and with a surfactant such as, for example, GAFAC® or TWEEN® 20). The reaction mixture is subjected to agitation by, for example, stirring or shaking. The temperature during the reaction is about 18° C. to about 25° C., or about room temperature. The reactants are subjected to agitation during the reaction by stirring or shaking, for example. The time period of the reaction is about 2 hours to about 24 hours, or about 15 to about 21, for example. The resulting particle (XI) may be subjected to one or more washing and purification techniques such as, for example, diafiltration, centrifugation and sonication, for example.

General Description of Assays for Cortisol

Some examples in accordance with the principles described herein are directed to methods of determining one or both of the presence and the amount of cortisol in a sample suspected of containing cortisol and may be referred to herein as "assays for cortisol." The methods comprise providing in combination in a medium a sample suspected of containing cortisol, a specific binding member for cortisol and a conjugate of 11-α-cortisol linked at the 3-position to an assay molecule. The combination is subjected to conditions for binding of the conjugate to the specific binding member for cortisol to form a complex. The amount of the complex is measured and the amount of the complex is related to the presence and/or amount of cortisol in the sample.

As used herein in reference to assays, the term "cortisol" refers to one or more of cortisol, hydrocortisone, and metabolites of cortisol, for example.

The specific binding member is a member of a specific binding pair, which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody, although other specific binding pairs such as biotin-avidin, hormones-hormone receptors, enzyme-substrate, nucleic acid duplexes, IgG-protein A, polynucleotide pairs such as DNA-DNA, DNA-RNA, for example, are not immunological pairs but are included within the scope of the term "sbp member."

Specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. Preferred binding partners are antibodies.

In some examples of assays in accordance with the principles described herein, the specific binding member for cortisol is an antibody for cortisol, which may be a complete immunoglobulin molecule or a fragment thereof. Antibodies include various classes and isotypes, such as IgA, IgD, IgE, IgG1, IgG2a, IgG2b and IgG3, and IgM, for example.

Fragments thereof may include Fab, Fv and F(ab')$_2$, Fab', and the like. In addition, aggregates, polymers, and conjugates of immunoglobulins or their fragments can be used where appropriate so long as binding affinity for cortisol is retained. Antibodies for cortisol may be prepared by techniques including, but not limited to, immunization of a host and collection of sera (polyclonal), preparing continuous hybrid cell lines and collecting the secreted protein (monoclonal) or cloning and expressing nucleotide sequences or mutagenized versions thereof coding at least for the amino acid sequences required for specific binding of natural antibodies, for example.

The sample to be analyzed is one that is suspected of containing cortisol. The samples may be biological samples or non-biological samples. Biological samples may be from a mammalian subject or a non-mammalian subject. Mammalian subjects may be, e.g., humans or other animal species. Biological samples include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum. Non-biological samples including, but not limited to, waste streams, for example, may also be analyzed using compounds in accordance with the principles described herein.

The sample can be prepared in any convenient medium, which may be, for example, an assay medium, which is discussed more fully below. In some instances a pretreatment may be applied to the sample such as, for example, to lyse blood cells. In some examples, such pretreatment is performed in a medium that does not interfere subsequently with an assay.

The combination in the medium is subjected to conditions for binding of the conjugate of 11-α-cortisol linked at the 3-position to an assay molecule to the specific binding member for cortisol to form a complex. The amount of the complex is measured where the amount of the complex is related to one or both of the presence and amount of cortisol in the sample.

An assay for cortisol can be performed either without separation (homogeneous) or with separation (heterogeneous) of any of the assay components or products. Heterogeneous assays usually involve one or more separation steps and can be competitive or non-competitive. Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling assays, for example.

One general group of immunoassays includes immunoassays using a limited concentration of a compound in accordance with the principles described herein. Another group of immunoassays involves the use of an excess of one or more of the principal reagents such as, for example, an excess of a compound in accordance with the principles described herein. Another group of immunoassays includes separation-free homogeneous assays in which a labeled reagent in accordance with the principles described herein modulates the label signal upon binding of a compound in accordance with the principles described herein to a specific binding member for cortisol, thus competing with cortisol that may be present in the sample.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The relevant portions of the above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"); the Affinity Chromium dioxide Mediated Immuno Assay ("ACMIA") assay format, which is described in U.S. Pat. Nos. 7,186,518, 5,147,529, 5,128,103, 5,158,871, 4,661,408, 5,151,348, 5,302,532, 5,422,284, 5,447,870, and 5,434,051, the disclosures of which are incorporated herein in their entirety; for example.

Other assays include acridinium ester label assays such as those discussed in U.S. Pat. Nos. 6,355,803; 6,673,560; 7,097,995 and 7,319,041, the relevant disclosures of which are incorporated herein by reference. A particular example of an acridinium ester label assay is an acridinium ester label immunoassay using paramagnetic particles as a solid phase ("ADVIA" immunoassay). Other assays include the sol particle immunoassay ("SPIA"), the disperse dye immunoassay ("DIA"); the metalloimmunoassay ("MIA"); the enzyme membrane immunoassays ("EMIA"); and luminoimmunoassays ("LIA"). Other types of assays include immunosensor assays involving the monitoring of the changes in the optical, acoustic and electrical properties of the present conjugate upon the binding of cortisol analyte. Such assays include, for example, optical immunosensor assays, acoustic immunosensor assays, semiconductor immunosensor assays, electrochemical transducer immunosensor assays, potentiometric immunosensor assays, amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In an example of a competitive heterogeneous assay, a support having an antibody for cortisol bound thereto is contacted with a medium containing the sample suspected of containing cortisol and a labeled conjugate in accordance with the principles described herein. Cortisol in the sample competes, for binding to the cortisol antibody, with the conjugate in accordance with the principles described herein bearing a detectable label. After separating the support and the medium, the label activity of the support or the medium is determined by conventional techniques and is related to the amount of cortisol analyte in the sample. In a variation of the above competitive heterogeneous assay, the support comprises a labeled conjugate in accordance with the principles described herein as the labeled reagent and cortisol antibody comprises a label.

In some examples, a sample to be analyzed is combined in an assay medium with an antibody for cortisol and labeled conjugate in accordance with the principles described herein. The medium is examined for one or both of the presence and amount of a complex comprising the labeled conjugate and the antibody for cortisol where the presence and/or the amount of such complex indicates the presence and/or amount of cortisol in the sample.

In some examples in accordance with the principles described herein, the sample to be analyzed is subjected to a pretreatment to release cortisol from endogenous binding substances such as, for example, plasma or serum proteins that bind cortisol such as, e.g., cortisol binding globulin (also known as corticosteroid binding globulin, transcortin, and CBG), and/or albumin. The release of cortisol from endogenous binding substances may be carried out, for example, by increasing the temperature of the sample to about 55° C. to about 65° C. for a period of about 0.5 hours to about 2 hours or about 1 hour to about 1.5 hours. In another approach, addition of a cortisol releasing agent to the sample may be employed to release cortisol from endogenous binding substances. Cortisol releasing agents include, but are not limited to, sodium salicylate and danazol, for example.

The conditions such as, for example, duration, temperature, pH and concentration of the releasing agent in the medium for carrying out the releasing actions are dependent on the nature of the endogenous binding substances, the nature of the sample, and the nature of the releasing agent, for example. In general, the conditions are sufficient to achieve the desired effect or function. In some examples in accordance with the principles described herein, an effective concentration of releasing agent is about 0.01 to about 20 mg/mL, or about 0.01 to about 10 mg/mL, or about 0.01 to about 5 mg/mL, or about 0.1 to about 20 mg/mL, or about 0.1 to about 10 mg/mL, or about 0.1 to about 5 mg/mL, or about 0.1 to about 1 mg/mL. The pretreatment of the sample to release cortisol from endogenous binding substances may be carried out as a separate step prior to conducting an assay or as a first step in an assay. In either case, one or more reagents may be required to stop the action of the releasing agent.

The conditions for conducting assays for cortisol include carrying out the assay in an aqueous buffered medium at a moderate pH, generally that which provides optimum assay sensitivity. The aqueous medium may be solely water or may include from 0.1 to about 40 volume percent of a cosolvent. The pH for the medium will be in the range of about 4 to about 11, or in the range of about 5 to about 10, or in the range of about 6.5 to about 9.5, for example. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the assay. Illustrative buffers include, by way of illustration and not limitation, borate, phosphate, carbonate, TRIS, barbital, PIPES, HEPES, MES, ACES, MOPS, and BICINE, for example. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, proteins may be included, such as, for example, albumins; organic solvents such as, for example, formamide; quaternary ammonium salts; polyanions such as, for example, dextran sulfate; binding enhancers, for example, polyalkylene glycols; polysaccharides such as, for example, dextran or trehalose. The medium may also comprise agents for preventing the formation of blood clots. Such agents are well known in the art and include, but are not limited to, EDTA, EGTA, citrate, heparin, for example. The medium may also comprise one or more preservatives such as, but not limited to, sodium azide, neomycin sulfate, PROCLIN® 300, Streptomycin, for example. The medium may additionally comprise one or more surfactants. Any of the above materials, if employed, is present in a concentration or amount sufficient to achieve the desired effect or function.

One or more incubation periods may be applied to the medium at one or more intervals including any intervals between additions of various reagents employed in an assay including those mentioned above. The medium is usually incubated at a temperature and for a time sufficient for binding of various components of the reagents and binding of cortisol in the sample to occur. Moderate temperatures are normally employed for carrying out the method and usually constant temperature, preferably, room temperature, during the period of the measurement. In some examples, incubation temperatures range from about 5° to about 99° C., or from about 15° C. to about 70° C., or from about 20° C. to about 45° C., for example. The time period for the incubation, in some examples, is about 0.2 seconds to about 24 hours, or about 1 second to about 6 hours, or about 2 seconds to about 1 hour, or about 1 minute to about 15 minutes, for example. The time period depends on the temperature of the medium and the rate of binding of the various reagents, which is determined by the association rate constant, the concentration, the binding constant and dissociation rate constant.

In an example of a method for determining cortisol in a sample suspected of containing cortisol, a combination is provided in a medium where the combination includes the sample, a releasing agent (if the sample has not been pretreated to release cortisol from endogenous binding substances), an antibody for cortisol, and a labeled conjugate in accordance with the principles described herein where the label is a poly(amino acid) label or a non-poly(amino acid) label. The medium is examined for one or both of the presence and amount of one or both of a complex comprising cortisol and the antibody for cortisol or a complex comprising the labeled compound and antibody for cortisol. The presence and/or the amount of one or both of the complexes indicates the presence and/or amount of cortisol in the sample.

Some known assays utilize a signal producing system (sps) that employs first and second sps members. The designation "first" and "second" is completely arbitrary and is not meant to suggest any order or ranking among the sps members or any order of addition of the sps members in the present methods. The sps members may be related in that activation of one member of the sps produces a product such as, e.g., light or an activated product, which results in activation of another member of the sps.

In some embodiments of assays, the sps members comprise a sensitizer such as, for example, a photosensitizer, and a chemiluminescent composition where activation of the sensitizer results in a product that activates the chemiluminescent composition. The second sps member usually generates a detectable signal that relates to the amount of bound and/or unbound sps member, i.e., the amount of sps member bound or not bound to the cortisol analyte being detected or to a conjugate in accordance with the principles described herein. In some examples in accordance with the principles described herein, one of either the sensitizer reagent or the chemiluminescent reagent comprises the present conjugate reagent, that is, a conjugate of 11-α-cortisol linked at the 3-position to an assay molecule, which in this example is a label.

In a particular example, an induced luminescence immunoassay may be employed. The induced luminescence immunoassay is referred to in U.S. Pat. No. 5,340,716 (Ullman), which disclosure is incorporated herein by reference. In one approach, the assay uses a particle having associated therewith a photosensitizer where a conjugate in accordance with the principles described herein comprises the particle (particle-conjugate reagent). The chemiluminescent reagent comprises an antibody for cortisol. The cortisol analyte competes with the particle-conjugate reagent for binding to the antibody for cortisol. If the cortisol analyte is present, the fewer is the number of molecules of particle-conjugate reagent that come into close proximity with the chemiluminescent reagent. Therefore, there will be a decrease in the assay signal. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of cortisol analyte present in the sample.

In another particular example of an induced luminescence immunoassay, the assay uses a particle having associated therewith a chemiluminescent conjugate where a conjugate in accordance with the principles described herein comprises the particle (particle-conjugate reagent). The photosensitizer reagent comprises an antibody for cortisol. The cortisol analyte competes with the particle-conjugate reagent for binding to the antibody for cortisol. If the cortisol analyte is present, the fewer is the number of molecules of particle-conjugate reagent that come into close proximity with the photosensitizer reagent. Therefore, there will be a decrease in the assay signal. The photosensitizer generates singlet oxygen and activates the chemiluminescent conjugate of the particle-conjugate reagent when the two labels are in close proximity. The activated chemiluminescent conjugate subsequently produces light. The amount of light produced is related to the amount of the complex formed, which in turn is related to the amount of cortisol analyte present in the sample.

In another particular example of an induced luminescence assay, a photosensitizer particle is employed that is conjugated to a binding partner for a small molecule such as, for example, avidin or streptavidin (which are binding partners for biotin). A conjugate in accordance with the principles described herein that comprises biotin (conjugate-biotin reagent where biotin is an assay molecule in this example) is also employed. A chemiluminescent reagent that comprises a specific binding member for cortisol is employed as part of the detection system. The reaction medium is incubated to allow the avidin or streptavidin of the photosensitizer particles to bind to the conjugate-biotin reagent by virtue of the binding between avidin and biotin and to also allow the specific binding member for the cortisol that is part of the chemiluminescent reagent to bind to the cortisol analyte or to the conjugate in accordance with the principles described herein that is now attached to the photosensitizer particles. Then, the medium is irradiated with light to excite the photosensitizer, which is capable in its excited state of activating oxygen to a singlet state. Because less of the chemiluminescent reagent is now in close proximity to the photosensitizer because of the presence of the cortisol analyte, there is less activation of the chemiluminescent reagent by the singlet oxygen and less luminescence. The medium is then examined for the presence and/or the amount of luminescence or light emitted, the presence thereof being related to the presence and/or amount of the cortisol analyte where a decrease in signal is observed in the presence of the cortisol analyte.

In another particular example of an induced luminescence assay, a photosensitizer particle is employed that is conjugated to a binding partner for a small molecule such as, for example, avidin or streptavidin (which are binding partners for biotin). Another assay reagent comprises a specific binding member for cortisol conjugated to biotin. A conjugate in accordance with the principles described herein is employed where the conjugate comprises a chemiluminescent particle as an assay molecule (chemiluminescent-conjugate reagent) is also employed. The reaction medium is incubated to allow the avidin or streptavidin of the photosensitizer particles to bind to the antibody-biotin reagent by virtue of the binding between avidin and biotin and to also allow the specific binding member for the cortisol to bind to cortisol if present in the sample and to the conjugate in accordance with the principles described herein that is part of the chemiluminescent-conjugate reagent. Then, the medium is irradiated with light to excite the photosensitizer, which is capable in its excited state of activating oxygen to a singlet state. Because less of the chemiluminescent-conjugate reagent is now in close proximity to the photosensitizer because of the presence of the cortisol analyte, there is less activation of the chemiluminescent reagent by the singlet oxygen and less luminescence. The medium is then examined for the presence and/or the amount of luminescence or light emitted, the presence thereof being related to the presence and/or amount of the cortisol analyte where a decrease in signal is observed in the presence of the cortisol analyte.

Another example, by way of illustration and not limitation, of an assay format for detection of cortisol is the ACMIA assay format. For the ACMIA assay format, a conjugate reagent in accordance with the principles described herein comprises chrome particles as an assay molecule (chrome particle-conjugate reagent), are employed as a first component. A second component is an antibody for cortisol. This antibody, crosslinked to a reporter enzyme (for example, (3-galactosidase) to form an antibody-enzyme conjugate, is added to a reaction vessel in an excess amount, i.e., an amount greater than that required to bind all of the cortisol analyte that might be present in a sample. A sample, which is previously subjected to treatment with a releasing agent, is treated with an antibody for cortisol, which binds to cortisol in the sample. The antibody-enzyme conjugate is mixed with sample in the medium to allow the cortisol analyte to bind to the antibody. Next, the chrome particle-conjugate reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of cortisol in the sample.

Another example of an assay for cortisol in accordance with the principles described herein is an acridinium ester label immunoassay using paramagnetic particles as a solid phase (ADVIA immunoassay). The detection system employed for this example of a cortisol assay includes a small molecule-labeled conjugate in accordance with the principles described herein (capture conjugate), binding partner for the small molecule-coated paramagnetic latex particles as a solid phase (SP), and an acridinium ester labeled antibody for cortisol (detection antibody). The small molecule may be, for example, biotin or fluorescein and the respective binding partner may be streptavidin or antibody for fluorescein. Cortisol in a patient sample competes with cortisol of the capture moiety for binding to the acridinium ester labeled detection anti-cortisol antibody. The sample suspected of containing cortisol is subjected to a pretreatment to release cortisol from endogenous binding substances. The assay may be carried out on a Centaur®, Centaur® XP or Centaur® CP apparatus (Siemens Healthcare Diagnostics Inc., Newark Del.) in accordance with the manufacturer's directions supplied therewith.

Another example of an assay for cortisol in accordance with the principles described herein is an acridinium ester label immunoassay using paramagnetic particles as a solid phase (ADVIA immunoassay). The detection system employed for this example of a cortisol assay includes a small molecule-labeled antibody for cortisol (capture antibody) as the biotin conjugate or capture conjugate, streptavidin-coated paramagnetic latex particles as a solid phase (SP), and an acridinium ester labeled conjugate in accordance with the principles described herein (detection hapten). Cortisol in a patient sample competes with the acridinium ester labeled detection hapten for binding with anti-cortisol antibody. The sample suspected of containing cortisol is subjected to a pretreatment with 1,8-ANS. The assay may be carried out on a Centaur®, Centaur® XP or Centaur® CP apparatus (Siemens Healthcare Diagnostics Inc., Newark Del.) in accordance with the manufacturer's directions supplied therewith. In variations of the above acridinium ester assays, the small molecule may be, for example, fluorescein in place of biotin and anti-fluorescein coated paramagnetic latex particles may be employed as the solid phase (SP).

The concentration of the cortisol analyte in a sample that may be assayed generally varies from about $10^{-5}$ to about $10^{-17}$ M, or from about $10^{-6}$ to about $10^{-14}$ M, for example. Considerations such as whether the assay is qualitative, semi-quantitative or quantitative (relative to the amount of the cortisol analyte present in the sample), the particular detection technique and the expected concentration of the cortisol analyte normally determine the concentrations of the various reagents.

The concentrations of the various reagents in the assay medium will generally be determined by the concentration range of interest of the cortisol analyte, the nature of the assay, and the like. However, the final concentration of each of the reagents is normally determined empirically to optimize the sensitivity of the assay over the range of interest. That is, a variation in concentration of cortisol analyte that is of significance should provide an accurately measurable signal difference. Considerations such as the nature of the signal producing system and the nature of the analytes normally determine the concentrations of the various reagents.

As mentioned above, the sample and reagents are provided in combination in the medium. While the order of addition to the medium may be varied, there will be certain preferences for some embodiments of the assay formats described herein. The simplest order of addition, of course, is to add all the materials simultaneously and determine the effect that the assay medium has on the signal as in a homogeneous assay. Alternatively, each of the reagents, or groups of reagents, can be combined sequentially. In some embodiments, an incubation step may be involved subsequent to each addition as discussed above. In heterogeneous assays, washing steps may also be employed after one or more incubation steps.

In one particular example, a method for determining cortisol comprises providing in combination in a medium a sample suspected of containing cortisol, a specific binding member for cortisol and a compound of the formula:

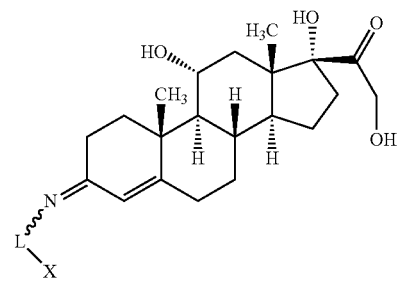

wherein L is a linking group, as described above, and X is a support or a member of a signal producing system. The combination is subjected to conditions for binding of the compound to the specific binding member for cortisol to form a complex. The amount of the complex is measured and the amount of the complex is related to the presence and/or amount of cortisol in the sample.

Examination Step

In a next step of an assay method, the medium is examined for the presence of a complex comprising the cortisol analyte and antibody for cortisol and/or a complex comprising a compound reagent in accordance with the principles described herein and antibody for cortisol. The presence and/or amount of one or both of the complexes indicates the presence and/or amount of the cortisol analyte in the sample.

The phrase "measuring the amount of a cortisol analyte" refers to the quantitative, semiquantitative and qualitative determination of cortisol. Methods that are quantitative, semiquantitative and qualitative, as well as all other methods for determining the cortisol analyte, are considered to be methods of measuring the amount of the cortisol analyte. For example, a method, which merely detects the presence or absence of the cortisol analyte in a sample suspected of containing the cortisol analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the cortisol analyte in the sample. The particular mode of detection depends on the nature of the signal producing system. As discussed above, there are numerous methods by which a label of a signal producing signal can produce a signal detectable by external means. Activation of a signal producing system depends on the nature of the signal producing system members.

Temperatures during measurements generally range from about 10° C. to about 70° C. or from about 20° C. to about 45° C., or about 20° C. to about 25° C., for example. In one approach standard curves are formed using known concentrations of cortisol analyte. Calibrators and other controls may also be used.

Luminescence or light produced from any label can be measured visually, photographically, actinometrically, spectrophotometrically, such as by using a photomultiplier or a photodiode, or by any other convenient means to determine the amount thereof, which is related to the amount of cortisol analyte in the medium. The examination for presence and/or amount of the signal also includes the detection of the signal, which is generally merely a step in which the signal is read. The signal is normally read using an instrument, the nature of which depends on the nature of the signal. The instrument may be, but is not limited to, a spectrophotometer, fluorometer, absorption spectrometer, luminometer, and chemiluminometer, for example.

Kits Comprising Reagents for Conducting Assays

A reagent comprising a conjugate of 11-α-cortisol linked at the 3-position to an assay molecule and/or a support, and other reagents for conducting a particular assay for a cortisol analyte may be present in a kit useful for conveniently performing an assay for the determination of a cortisol analyte. In some embodiments a kit comprises in packaged combination a biotin-binding partner such as, for example, avidin or streptavidin, associated with a particle, biotinylated conjugate in accordance with the principles described herein and a labeled antibody for the cortisol analyte. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional specific binding pair members, signal producing system members, and ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay using a compound reagent in accordance with the principles described herein. The kit can further include a written description of a method utilizing reagents that include a compound reagent in accordance with the principles described herein.

Explanation of Terms and Phrases

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The term "alkyl" includes those alkyl groups of a designated number of carbon atoms of either a straight, branched, or cyclic configuration. Examples of "alkyl" include, but are not limited to, methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, for example.

The term "alkenyl" includes hydrocarbon chains of a specified number of carbon atoms of either a straight- or branched-configuration and at least one carbon-carbon double bond, which may occur at any point along the chain, examples of which include, but are not limited to, ethenyl, propenyl, butenyl, pentenyl, dimethyl pentenyl, for example.

The term "alkynyl" refers to a straight or branched chain hydrocarbon of a specified number of carbon atoms containing at least one carbon-carbon triple bond, including, but not limited to, ethynyl, 1-propynyl, 2-propynyl, 1-butynyl, and 2-butynyl, for example.

The term "alkoxy" includes alkyl groups of a designated number of carbon atoms of either a straight, branched or cyclic configuration wherein the alkyl group includes an ether oxygen for linking to a parent compound.

The bond symbol " ∼ " used in the formulas herein refers to stereoisomer " ▬ " or to stereoisomer " ⅢⅢ " or to mixtures of the two stereoisomers.

The following discussion is directed to specific examples in accordance with the principles described herein by way of illustration and not limitation; the specific examples are not intended to limit the scope of the present disclosure and the appended claims. Numerous modifications and alternative compositions, methods, and systems may be devised without departing from the spirit and scope of the present disclosure.

Examples

Unless otherwise indicated, materials in the experiments below may be purchased from the Sigma-Aldrich Chemical Corporation (St. Louis Mo.) or Fluka Chemical Corporation (Milwaukee Wis.). Parts and percentages disclosed herein are by weight to volume unless otherwise indicated.

Definitions mg=milligram
g=gram(s)
ng=nanogram(s)

mL=milliliter(s)
µL=microliter(s)
dL=deciliter(s)
µmol=micromolar
° C.=degrees Centigrade
min=minute(s)
sec=second(s)
hr=hour(s)
w/v=weight to volume
TLC=thin layer chromatography
HPLC=high performance liquid chromatography
EDA=ethylenediamine
EDAC=N-(3-Dimethylaminopropyl)-N'-ethylcarbodiimide hydrochloride
EDTA=ethylenediaminetetraacetic acid
sulfoNHS or SNHS=sulfo N-hydroxysuccinimide
EtOAc=ethyl acetate
NaOAc=sodium acetate
DMF=dimethylformamide
DMSO=dimethylsulfoxide
MeOP=1-methoxy-2-propanol
MES=2-(N-morpholino)ethanesulfonic acid
Hapten Wash Buffer=50 mM HEPES, 300 mM NaCl, 1 mM EDTA, 0.01% neomycin sulfate, 0.1% TRITON® 405X and 0.15% PROCLIN0 300, pH7.2
DI=distilled
UPA=Ultra Particle Analyzer
LOCI=luminescent oxygen channeling immunoassay
BSA=bovine serum albumin
BGG=bovine gamma globulin
mIgG=mouse immunoglobulin
MS=mass spectrometry
TLC=thin layer chromatography
SD=standard deviation
CV=coefficient of variation Preparation of EPRM-EDA Beads EPRM beads (2000 mg, 20.0 mL) are added to a 40-mL vial. The EPRM beads are prepared by a procedure similar to that described in U.S. Pat. No. 7,179,660 and the chemiluminescent compound is 2-(4-(N,N, di-tetradecyl)-anilino-3-phenyl thioxene with europium chelate. EDA (800 mg, 890 µL) is combined with 10 mL MES pH 6 buffer (the "Buffer") and about 4.2 mL 6N HCl. The pH of the mixture is, or is adjusted to be, about 6.9. The EDA solution is added to the EPRM beads with vortexing and the mixture is rocked at room temperature for 15 min. Sodium cyanoborohydride (400 mg) is combined in a 15 mL vial with 10 mL DI water and the combination is added to the bead mixture from above. The mixture is shaken at 37° C. for 18-20 hours. The beads are transferred to six 40 mL centrifuge tubes. MES buffer is added to bring the volume to 35 mL and the mixture is centrifuged at 19,000 rpm for 30 min. The supernatant is decanted and the beads are re-suspended in 2 mL of the Buffer with a stir-rod and additional Buffer is added to 35 mL. The mixture is sonicated at 18 Watts power for 30 sec, using ice to keep the mixture cold. The wash/sonication step is performed 4 times to remove all activation chemical. After the last MES Buffer centrifugation, 2 mL of the Buffer containing 5% MeOP and 0.1% Tween® 20 (the "second Buffer") is added to the tubes for the re-suspension step. Additional second buffer is added to 35 mL before sonication. The bead suspension is centrifuged at 19,000 rpm for 30 min. The supernatant is discarded. The final sonication used 12 mL of the second Buffer in each tube to give a 25 mg/mL dilution. Particle size is 277 nm as determined on a UPA instrument.

The EPRM chemibead is prepared in a manner similar to the method described in U.S. Pat. No. 6,153,442 and U.S. Patent Application Publication No. 20050118727A, the relevant disclosures of which are incorporated herein by reference. The EPRM chemibead comprises an aminodextran inner layer and a dextran aldehyde outer layer having free aldehyde functionalities. See, for example, U.S. Pat. Nos. 5,929,049, 7,179,660 and 7,172,906, the relevant disclosures of which are incorporated herein by reference. The reaction is carried out at a temperature of about 0 to about 40° C. for a period of about 16 to about 64 hours at a pH of about 5.5 to about 7.0, or about 6, in a buffered aqueous medium employing a suitable buffer such as, for example, MES. The reaction is quenched by addition of a suitable quenching agent such as, for example, carboxymethoxyamine hemihydrochloride (CMO), and subsequent washing of the particles.

Aldehyde groups on the outer dextran aldehyde layer are reacted with ethylene diamine under reductive amination conditions to form reagent EPRM-EDA having pendant moieties comprising an ethylene chain and a terminal amine group. The reductive amination conditions include the use of a reducing agent such as, for example, a metal hydride. The reaction is carried out in an aqueous medium at a temperature during the reaction of about 20° C. to about 100° C. for a period of about 1 hr to about 48 hr.

Synthesis of 11-α-cortisol-3-carboxymethoxyoxime (VIII)

A mixture of 49 mg (14 µmol) 11-α-cortisol (Steraloids, Inc., Newport R.I.), 18 mg (16 µmol) CMO (Carboxymethoxyoxime hemihydrochloric acid), 20 mg NaOAc in 1 mL anhydrous methanol in a 5 ml flask was stirred at room temperature for 22 h. TLC (EtOAc:Hexane=2:1) showed no starting material left. The solvent was removed as much as possible under vacuum. EtOAc (50 ml) and 1 ml DI water were added to the residue, and the mixture was then stirred for 20 min. After separation, the organic phase was washed three times with 3×2 ml brine. The organic phase was dried with anhydrous Na$_2$SO$_4$ and filtered. Solvent was removed using a rotary evaporator and the resulting material was subjected to drying under high vacuum to give 42 mg of crude product, which was confirmed to be 11-α-cortisol-3-carboxymethoxyoxime (VIII) by MS.

Coupling of EPRM-EDA Beads and 11-α-Cortisol-3-Carboxymethoxyoxime (VIII) to Give Particle Reagent XI Referring to FIG. 5, 2.7 mg of 11-α-cortisol-3-carboxymethoxyoxime (VIII), prepared as described above, was added to a 2-mL vial followed by addition of 135 µL dry DMSO (20 mg/mL). The above solution (25 µL) (0.5 mg) was added to a 2-mL vial followed by addition of 975 µL of a EDAC/SNHS solution (0.5 mg/mL) which was previously prepared by combining EDAC (13.8 mg) and SNHS (19.5 mg) plus 4.6 mL dry DMSO (3 mg/mL) in a 5-mL vial. The mixture was allowed to rotate at room temperature for 18 hr to give activated compound IX (FIG. 5).

To a 2-mL centrifuge tube was added 0.5 mL (50 mg) EPRM-EDA beads, prepared as described above, followed by 65 µL 1.6% GAFAC® surfactant solution (0.15%) and the mixture was subjected to vortexing. To a small test tube was added 126 µL DMSO followed by 0.15 µL (0.0075 mg) activated compound IX. The DMSO/activated compound IX solution was added to the bead mixture (subjected to vortexing during addition). The resulting concentration of DMSO to the beads was 20% DMSO. The centrifuge tube was allowed to rotate overnight at room temperature.

The resulting beads were washed by transferring to a 40-mL centrifuge tubes. MES pH6 buffer containing 10% MeOP and 1% GAFAC® surfactant solution (the "MeOP Buffer") was added to bring tubes to 35 mL. The tube was centrifuged at 19,000 rpm for 30 min. Supernatant was decanted. Beads were re-suspended in 10 mL of the MeOP Buffer with a stir-rod. More of the MeOP Buffer was added to bring the volume in the tubes to 35 mL. The tube was kept cold with ice and the contents of the tube were sonicated at 18-21 Watts power for 60 sec. The beads were centrifuged as above with a total of eight MeOP Buffer washes being performed. After the last MeOP Buffer wash, the beads were resuspended in 10 mL Hapten Wash Buffer instead of the MeOP Buffer as above with two more washes being performed. The beads were resuspended in sufficient Hapten Wash Buffer to give 12 mg/mL suspension. Beads were sonicated at 50% power (cup sonicator) for 30 sec. Particle size was tested on UPA instrument and found to be 286 nm. Percent solids assay was performed and bead lot brought up to 10 mg/mL with Hapten Wash Buffer pH7.2. Yield was 38.8 mg.

Assay for Cortisol Analyte

Assays were carried out on a DIMENSION® VISTA® analyzer (Siemens Healthcare Diagnostics Inc., Deerfield, Ill.) following the protocol for a LOCI assay and using sample solutions containing varying amounts of cortisol (as an example of measuring total cortisol in a sample). In this example, the assay uses, as a chemiluminescent reagent, a label particle-conjugate ("chemibead(s)") in accordance with the principles described herein and prepared as described above where the label of the particle-conjugate is a chemiluminescent compound contained in a latex particle. Samples were reacted first with a biotinylated monoclonal antibody against cortisol and then with chemibeads. The chemibeads bind to the fraction of the monoclonal antibody binding sites that is not occupied by analyte from the sample. Subsequently, streptavidin coupled sensitizer beads are added to the reaction mixture. This leads to the formation of chemibead/sensibead pairs whose concentration is inversely related to the concentration of cortisol. Upon illumination at 680 nm, the sensitizer beads generate singlet oxygen which diffuses into the chemibeads which are paired with sensibeads, reacts with the olefinic dye and triggers a chemiluminescent signal at approximately 612 nm which is inversely related to the analyte concentration.

The streptavidin-sensitizer bead ("sensibead(s)") was prepared using a method analogous to that described in U.S. Pat. Nos. 6,153,442, 7,022,529, 7,229,842 and U.S. Patent Application Publication No. 20050118727A. The photosensitizer was bis-(trihexyl)-silicon-t-butyl-phthalocyanine. The concentration of sensibead reagent was 250 µg/mL in HEPES buffer, pH 8.0 containing 342.2 mM NaCl, 1.16 mM EDTA, 1.2 mg/mL dextran T-500, 0.12% detergent and preservatives. The EPRM-EDA-25-OH Cortisol$_3$ particle reagent VI prepared as described above was employed as a "chemibead reagent" at a concentration of 25 µg/mL in HEPES buffer, pH 7.2, containing 300 mM NaCl, 16 mg/mL BSA, 1 mM EDTA, 1 mg/mL dextran T-500, 0.1% detergent and preservatives.

The biotinylated antibody reagent is prepared using monoclonal antibody specific for cortisol (sheep monoclonal from AbD Serotec, Raleigh N.C.) and biotinylating amine groups of the antibody by reaction with NHS-PEO$_4$-biotin (Pierce Chemical Company, Rockford Ill.) in a manner similar to that described in U.S. Patent Application Publication No. 2009/0258435A1, the relevant portions of which are incorporated herein by reference. The biotinylated antibody reagent is prepared in HEPES buffer pH 7.2 containing 150 mM NaCl and 16 mg/mL BSA, 1 mg/mL mIgG and 2 mg/mL BGG where the concentration of biotinylated antibody reagent is 1000 ng/mL.

The assays were also carried out as above with the exception that 11-β-cortisol particle reagent (β-reagent) was employed in place of 11-α-cortisol particle reagent XI for purposes of comparison. The 11-β-cortisol particle reagent was prepared in a manner similar to that described above for 11-α-cortisol particle reagent XI.

At time t=zero sec, 20 µL biotinylated antibody reagent and 60 µL water were added to a reaction vessel. Sample (cortisol calibrators) 12 µL, was added 21.6 seconds later, followed by 20 µL water. At t=241.2 seconds, 20 µL chemibead reagent (α-reagent XI or (β-reagent) was added followed by 20 µL of water. Sensibead reagent was then dispensed at 903.6 seconds. Measurements were taken 1263.6 seconds after initiation of the reaction sequence. The results are summarized in Table 1 below.

TABLE 1

| | kcounts | |
|---|---|---|
| Cortisol (µg/dL) | α-reagent XI | β-reagent |
| 0 | 2652 | 2777 |
| 1.4 | 2190 | 2443 |
| 4.2 | 1550 | 1982 |
| 12.0 | 742 | 1180 |
| 77.7 | 65 | 177 |

As can be seen from Table 1, the α-reagent XI chemibead reagent in accordance with the principles described herein gave consistently greater separation in signal counts compared to the β-reagent chemibead reagent.

Figure 6:
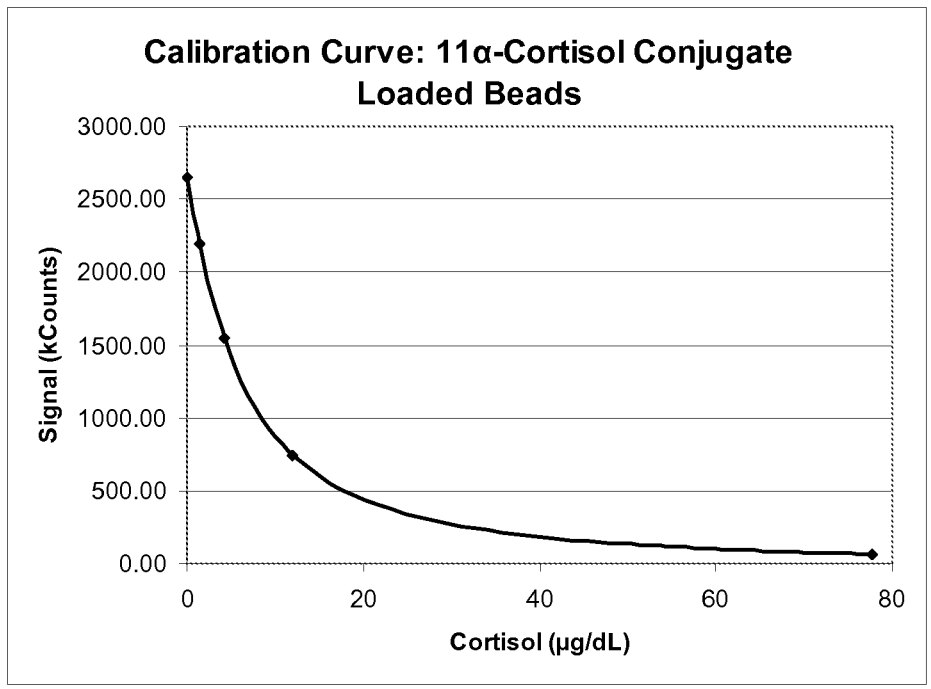
FIG. 6 is a graphic depiction of signal (calibration) curve for an assay conducted using an example of an 11-α-cortisol conjugate in accordance with the principles described herein.
Figure 7:
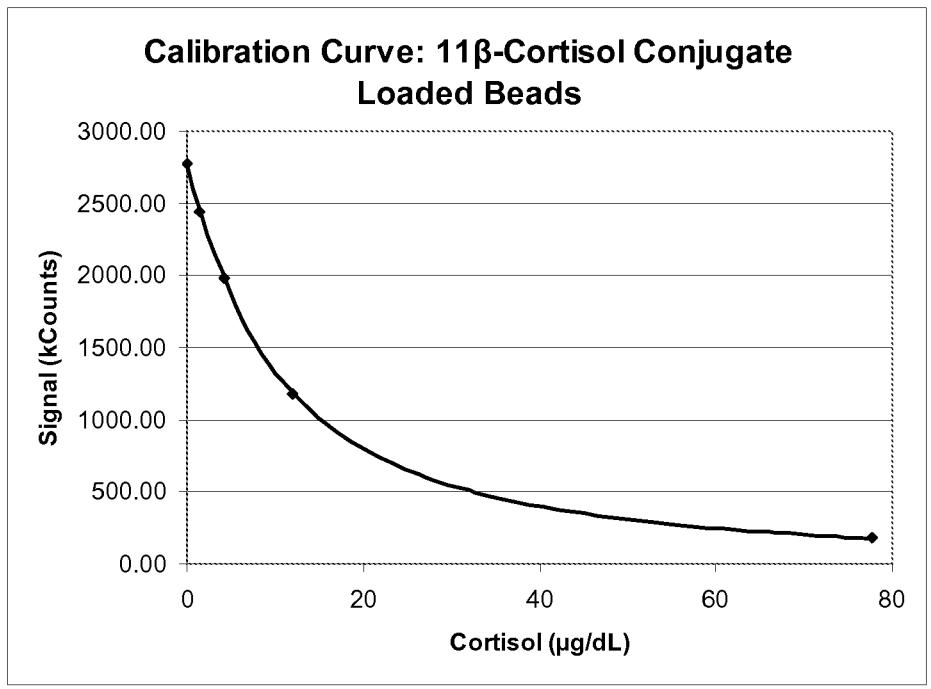
FIG. 7 is a graphic depiction of signal (calibration) curve for an assay conducted using an example of an 11-β-cortisol conjugate not in accordance with the principles described herein.

In addition, the shape of the signal (calibration) curve was improved for the α-reagent XI chemibead reagent in accordance with the principles described herein (FIG. 6) compared to that for the β-reagent chemibead reagent (FIG. 7) especially in the low end of the calibrator cortisol concentration. As can be seen there is a steeper decline in the curve for the α-reagent XI chemibead reagent in accordance with the principles described herein (FIG. 6) compared to that for the β-reagent chemibead reagent (FIG. 7).

Furthermore, zero level sample recovery (stripped human serum) is improved using the α-reagent XI chemibead reagent in accordance with the principles described herein compared to that for the β-reagent chemibead reagent. Results obtained are summarized in Table 2 below. The results indicate that the reduction of sample matrix effects when using the α-reagent XI chemibead reagent allowed for improved low end sensitivity and more accurate measurement of samples containing zero or low amounts of cortisol.

TABLE 2

| Conjugate | Cortisol (µg/dL) |
|---|---|
| α-reagent XI | −0.1 |
| β-reagent | −0.6 |

A precision study was also carried out using the α-reagent XI chemibead reagent in accordance with the principles described herein compared to the β-reagent chemibead reagent. The results show that low end precision is improved in a five-day ANOVA study of human serum samples when using the α-reagent XI chemibead reagent in accordance with the principles described herein compared to that for the β-reagent chemibead reagent. The ANOVA study is carried out over five days, running N=5 replicate measurements per sample per day, for a total of N=25 measurements per sample. The results are summarized in Table 3.

TABLE 3

|  |  | Sample | | | |
| --- | --- | --- | --- | --- | --- |
|  |  | 2B + 1A | 2A | 5A | 7A |
| α-reagent XI | | | | | |
| Mean cortisol (μg/dL) | | 0.7 | 1.6 | 12.3 | 44.0 |
| Repeatability | SD: | 0.04 | 0.06 | 0.15 | 0.49 |
|  | % CV: | 6.3 | 3.5 | 1.2 | 1.1 |
| Within-Lab | SD: | 0.06 | 0.10 | 0.19 | 0.69 |
|  | % CV: | 8.7 | 5.9 | 1.5 | 1.6 |
| β-reagent | | | | | |
| Mean cortisol (μg/dL) | | 0.4 | 1.9 | 12.5 | 43.0 |
| Repeatability | SD: | 0.07 | 0.09 | 0.14 | 0.61 |
|  | % CV: | 21.1 | 4.8 | 1.2 | 1.4 |
| Within-Lab | SD: | 0.08 | 0.12 | 0.19 | 0.69 |
|  | % CV: | 23.7 | 6.4 | 1.5 | 1.6 |

In Table 3, 2B+1A means a 1:1 mixture of internally prepared cortisol serum samples 2B and 1A; 2A means internally prepared cortisol serum sample 2A; 5A means internally prepared cortisol serum sample 5A; and 7A means internally prepared cortisol serum sample 7A. All samples were prepared, divided into aliquots and frozen prior to study initiation and fresh samples aliquots were thawed on each test day.

All publications and patent applications cited in this specification are herein incorporated by reference as if each individual publication or patent application were specifically and individually indicated to be incorporated by reference.

It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A compound of the formula:

wherein:
L is a linking group that is —O—$(CH_2)_p$—C(O)—NH—$(CH_2)_r$— and X is a support or a member of a signal producing system, and wherein the OH group at carbon 11 is α and wherein p is an integer of 1 to 10 and r is an integer of 1 to 10.

2. The compound according to claim 1 wherein X is a member of a signal producing system selected from the group consisting of particles, fluorescent compounds, chemiluminescent compounds, sensitizers, enzymes, and radiolabels.

3. The compound according to claim 1 wherein L is —O—$(CH_2)_p$—C(O)—NH—$(CH_2)_r$— wherein p is 1 and r is 1 and X is a particulate support.

4. The compound according to claim 1 wherein X is a particulate support that comprises a chemiluminescent compound or a photosensitizer.

5. A method of determining in a sample the presence and/or amount of cortisol, the method comprising:
    (a) providing in combination in a medium:
        (i) a sample suspected of containing cortisol,
        (ii) the compound according to claim 1 wherein X is a member of a signal producing system, and
        (iii) an antibody specific for cortisol;
    (b) subjecting the combination to conditions for binding of the compound of claim 1 to the antibody to form a complex, and
    (c) measuring the amount of the complex, the amount of the complex being inversely related to the presence and/or amount of cortisol in the sample.

6. The method according to claim 5 wherein the member of a signal producing system comprises a particle.

7. A method of determining in a sample the presence and/or amount of cortisol, the method comprising:
    (a) providing in combination in a medium:
        (i) a sample suspected of containing cortisol,
        (ii) a conjugate of 11-α-cortisol linked to an assay molecule, and
        (iii) an antibody specific for cortisol;
    (b) subjecting the combination to conditions for binding of the conjugate to the antibody for cortisol to form a complex; and
    (c) measuring the amount of the complex, the amount of the complex being inversely related to the presence and/or amount of cortisol in the sample wherein the conjugate has the formula:

wherein:
L is a linking group that is —O—$(CH_2)_p$—C(O)—NH—$(CH_2)_r$— and X is a support or a member of a signal producing system and wherein p is and integer of 1 to 10 and r is an integer of 1 to 10.

8. The method according to claim 7 wherein X is a member of a signal producing system selected from the group consisting of particles, fluorescent compounds, chemiluminescent compounds, sensitizers, enzymes, and radiolabels.

9. The method according to claim 7 wherein L is —O—$(CH_2)_p$—C(O)—NH—$(CH_2)_r$— wherein p is 1 and r is 1 and X is a particulate support.

* * * * *